(12) United States Patent
Tsuchikawa et al.

(10) Patent No.: US 7,763,237 B2
(45) Date of Patent: Jul. 27, 2010

(54) ULTRAVIOLET PROTECTIVE PREPARATION AND COSMETICS CONTAINING THE SAME

(75) Inventors: Koji Tsuchikawa, Kanagawa (JP); Keiichi Oyama, Kanagawa (JP)

(73) Assignee: The Nisshin OilliO Group, Ltd., Tokyo (JP)

(*) Notice: Subject to any disclaimer, the term of this patent is extended or adjusted under 35 U.S.C. 154(b) by 151 days.

(21) Appl. No.: 10/575,260

(22) PCT Filed: Oct. 6, 2004

(86) PCT No.: PCT/JP2004/015110
§ 371 (c)(1),
(2), (4) Date: Jan. 29, 2007

(87) PCT Pub. No.: WO2005/034899
PCT Pub. Date: Apr. 21, 2005

(65) Prior Publication Data
US 2007/0264207 A1 Nov. 15, 2007

(30) Foreign Application Priority Data
Oct. 10, 2003 (JP) .............................. 2003-352568

(51) Int. Cl.
*A61K 8/00* (2006.01)
*A61K 8/18* (2006.01)
*A61Q 17/04* (2006.01)
(52) U.S. Cl. .......................... 424/59; 424/61; 424/401; 424/63; 424/64
(58) Field of Classification Search .................. 424/59, 424/61, 63, 64
See application file for complete search history.

(56) References Cited

U.S. PATENT DOCUMENTS

| | | | | | |
|---|---|---|---|---|---|
| 4,254,104 | A | * | 3/1981 | Suzuki | 514/785 |
| 5,362,482 | A | * | 11/1994 | Yoneyama et al. | 424/69 |
| 5,849,272 | A | * | 12/1998 | Baba et al. | 424/59 |
| 5,968,531 | A | * | 10/1999 | Miyoshi et al. | 424/401 |
| 2002/0160023 | A1 | * | 10/2002 | Bagdi et al. | 424/401 |

FOREIGN PATENT DOCUMENTS

| | | |
|---|---|---|
| JP | 10-175819 A | 6/1998 |
| JP | 2000-219617 A | 8/2000 |
| JP | 2003-212747 A | 7/2003 |
| JP | 2004-217613 A | 8/2004 |
| WO | WO 02/11691 * | 2/2002 |
| WO | WO 02/078650 A1 | 10/2002 |

* cited by examiner

Primary Examiner—Johann R Richter
Assistant Examiner—Danielle Sullivan
(74) Attorney, Agent, or Firm—Sughrue Mion, PLLC

(57) ABSTRACT

An ultraviolet protective preparation comprising an ester prepared from glycerol and/or a condensate thereof, a straight-chain saturated fatty acid having 2 to 28 carbon atoms, and an aliphatic saturated dibasic acid having 12 to 28 carbon atoms, an oil liquid or pasty at ordinary temperatures which consists of an ester of a mono- to hexa-carboxylic acid having 2 to 36 carbon atoms with a mono- to hexa-hydric alcohol having 1 to 36 carbon atoms, and an ultraviolet protective powder in prescribed portions; and cosmetics containing the ultraviolet protective preparation. The invention provides an ultraviolet protective preparation which is improved in the dispersion stability of ultraviolet protective powder such as titanium dioxide or zinc oxide while keeping the handleability and the ability to give cosmetics excellent in organoleptic properties and storage stability; and cosmetics excellent in organoleptic properties and storage stability.

13 Claims, No Drawings

ULTRAVIOLET PROTECTIVE PREPARATION AND COSMETICS CONTAINING THE SAME

TECHNICAL FIELD

The present invention relates to an ultraviolet protective preparation and cosmetics containing the ultraviolet protective preparation, and, particularly, to an ultraviolet protective preparation superior in the dispersion stability of an ultraviolet protective powder and in handling characteristics when it is formulated in cosmetics by using a specified ester compound, a specified ester oil and the ultraviolet protective powder and to cosmetics containing the ultraviolet protective preparation.

BACKGROUND ART

In recent years, many sunscreens and cosmetics having a sunscreening effect have been used even in daily life because the adverse influence of ultraviolet rays on the human body has been well known and because of women's desire to keep the skin white. Along with this, a class of users of sunscreens or cosmetics having a sunscreening effect have spread. These cosmetics have come to be used for not only women who are anxious about their skins but also even babies and various products are being put on the market.

An ultraviolet absorber and an ultraviolet diffusing agent are formulated in these sunscreens and cosmetic shaving a sunscreening effect to protect the skin from ultraviolet rays. Synthetic compounds are mainly used as ultraviolet absorbers and examples of these synthetic ultraviolet absorbers include benzophenones, paraaminobenzoic acids, sinnamates, salicylates, dibenzoylmethanes and benzotriazoles. The amount of these ultraviolet absorbers to be compounded in a cosmetic is regulated and it is known that these ultraviolet absorbers have safety problems such as irritation to the skin. Also, these ultraviolet absorbers differ from each other in the wavelength of ultraviolet rays at which these absorbers exhibit maximum absorption depending on their structures. It is therefore necessary that these ultraviolet absorbers are used in combinations of several types and in combination with an ultraviolet diffusing agent. Moreover, in the case of ultraviolet absorbers having poor solubility in water or oily agents, there is the case where crystals precipitate and it is therefore difficult to formulate these absorbers in cosmetics.

On the other hand, an ultraviolet protective powder, for example, inorganic pigments such as titanium dioxide and zinc oxide is used in an ultraviolet diffusing agent. These inorganic pigments are chemically or physically stable and have high safety and cut off ultraviolet rays physically, thereby making it possible to protect the skin from a wide range of ultraviolet rays. These inorganic pigments also have the effect of an ultraviolet absorber due to the absorption resulting from the bandgap transition of electrons excited from the valence electron band to the conduction band by light energy.

When the ultraviolet protective powder is formulated in a cosmetic, dust is generated and scattered in a step of dispersing the powder in a dispersion medium. Therefore, products obtained by dispersing the ultraviolet protective powder in water or oil in advance are being put on the market to protect operators from suffering from respiratory disorders, to prevent other products and working fields from being contaminated with the dust and further to improve laborsaving in the manufacturing stage and handling characteristics.

The ultraviolet protective powder is sedimented and separated in a liquid dispersion and also solidified. It is known that the stability of a dispersion is usually improved by increasing the viscosity of the dispersion and a dispersion having a solid clay form obtained by excessively increasing the viscosity based on this fact is also being put on the market. However, such a dispersion having a solid clay form poses the handling problem that it is handled with difficulty when it is formulated in a cosmetic and it has poor dispersibility in a cosmetic.

Also, these dispersions have the problem that dispersion stability is deteriorated at lower temperatures or higher temperatures or along with a variation in temperature because the ultraviolet protective powder is different from the dispersion medium in thermal expansion coefficient and shrinkage factor.

As the method of dispersing the ultraviolet powder, a method of adding a dispersant is usually used. Examples of the dispersant include, besides a dispersion solution comprising using a glucose fatty acid ester having an acyl group having 10 to 14 carbon atoms (see Patent document 1), dispersants such as diglyceril monoisostearate, diglyceril diisostearate, glyceryl monoisostearate, polyoxyethyleneglyceryl isostearate having a HLB of 8 or less, polyoxyethylene glycol isostearate having a HLB of 8 or less, dextrin fatty acid ester, crosslinking type methylpolysiloxane, cellulose, methyl cellulose, ethyl cellulose, hydroxypropyl cellulose, polyhydroxystearic acid, polyhydroxycarboxylic acid, ethoxylated phosphate and reactive organic silicone (see, for example, Patent documents 2, 3 and 4).

Also, a pigment dispersion is disclosed which comprises a dispersant mixture containing an ester oil, an alkyl and/or alkenyl oligoglucoside and polyol poly-12-hydroxystearate (see, for example, Patent document 5).

As a method using no dispersant, there is a method in which the surface treatment of a microparticle ultraviolet protective powder is specified (see Patent document 6).

Patent document 1: Publication of JP-A No. 3-15463.1
Patent document 2: Publication of JP-B No. 6-61457
Patent document 3: Publication of JP-A No. 2001-58935
Patent document 4: Publication of JP-A No. 2002-80771
Patent document 5: Publication of Japanese Patent Application National Publication (Laid-open) No. 2001-524504
Patent document 6: Publication of JP-A No. 2002-80748

Patent document 1 relates to a solvent type or water-type pigment dispersion, which is, however, limited in use for w/c type sunscreening cosmetics that are main current and have high water resistance.

Also, in Patent documents 2 to 4, a dispersant is used to thereby improve the dispersibility of microparticle ultraviolet protective powder in oil and the like. However, in these references, the powder is inferior in dispersing stability at high temperatures or low temperatures or when the temperature is varied or when it is stored for a long time. Also, there is the case where coagulation arises and the emulsion is made unstable when the powder is formulated in a cosmetic, and finally, only insufficient dispersibility is obtained, so that a desired ultraviolet protective effect is not obtained.

Also, in Patent document 5, the amount of the ultraviolet protective powder to be compounded is as small as 0.1% to 5%, which is a concentration not enough to produce a sunscreen having a high ultraviolet protective effect by only the inorganic ultraviolet protective powder. In Patent document 6, problems, for example, the occurrence of coagulation when the powder is dispersed in an oil agent still remains though this depends on the formulation.

Accordingly, the present invention relates to an ultraviolet protective preparation which allows ultraviolet protective powder such as titanium dioxide and zinc oxide to disperse stably in an ultraviolet protective preparation and is superior in handling characteristics and dispersibility in a cosmetic and also relates to an ultraviolet protective preparation-containing cosmetic having a high function and storage stability.

DISCLOSURE OF THE INVENTION

The inventors of the present invention have made earnest studies repeatedly to solve the above problem and as a result, found that the above problem can be solved by combining an ester compound produced from glycerin and/or its condensate, straight-chain saturated fatty acid having 2 to 28 carbon atoms and an aliphatic saturated dibasic acid having 12 to 28 carbon atoms and a specified ester oil with an ultraviolet protective powder. The present invention was thus completed.

Accordingly, the present invention relates to an ultraviolet protective preparation comprising 0.1 to 10% by weight of an ester compound, 39.9 to 89.9% by weight of an ester oil and 10 to 50% by weight of an ultraviolet protective powder, wherein the ester compound is an ester compound produced from glycerin and/or its condensate, a straight-chain saturated fatty acid having 2 to 28 carbon atoms and an aliphatic saturated dibasic acid having 12 to 28 carbon atoms and the ester oil is an oil agent which has a liquid or paste form at normal temperature and is produced from a carboxylic acid having a monovalent to hexavalent carboxyl group and 2 to 36 carbon atoms and an alcohol having monohydric to hexahydric hydroxyl group and 1 to 36 carbon atoms, to attain the above object.

Also, the present invention relates to a cosmetic comprising the above ultraviolet protective preparation to attain the above object.

The present invention has the structure as mentioned above and has the inventive effect as described below.

The present invention can provide an ultraviolet protective preparation superior in the dispersion stability of an ultraviolet protective powder, dispersion stability at high temperatures, dispersion stability at low temperatures, dispersion stability under varied temperature conditions, dispersibility in a cosmetic and handling characteristics.

Also, the ultraviolet protective preparation of the present invention may be used in any of cosmetics including oil types, W/O type emulsions and O/W type emulsions. At this time, the content of the ultraviolet protective powder in the ultraviolet protective preparation can be controlled in a wide range from 10 to 50% by weight and it is therefore possible to contain the ultraviolet protective powder in such an amount as to enable production of an ultraviolet protective effect required for a cosmetic.

Also, the present invention can provide a cosmetic which not only can impart a proper SPF (Sun Protection Factor: sunscreening index) and a proper PA (Protection Grade of OVA) and but also has high storage stability without any loss of functionality.

It is to be noted that the dispersion stability of the ultraviolet protective preparation means the dispersion stability of the ultraviolet protective powder in the ultraviolet protective preparation. Also, the storage stability of the emulsion cosmetic means the emulsion stability of the emulsion cosmetic with time.

BEST MODE FOR CARRYING OUT THE INVENTION

The present invention will be explained in detail below.
The ultraviolet protective preparation of the present invention is an agent comprising:
an ester compound produced from glycerin and/or its condensate, a straight-chain saturated fatty acid having 2 to 28 carbon atoms and an aliphatic saturated dibasic acid having 12 to 28 carbon atoms;
an ester oil which is an oil agent which has a liquid or paste form at normal temperature and is produced from a carboxylic acid having a monovalent to hexavalent carboxyl group and 2 to 36 carbon atoms and an alcohol having monohydric to hexahydric hydroxyl group and 1 to 36 carbon atoms; and
an ultraviolet protective powder in each specified amount, (Ester Compound)

Although no particular limitation is imposed on the above glycerin and glycerin condensate having a mean degree of polymerization of 2 or more which are used as the raw material of the ester compound to be formulated in the present invention, they are preferably glycerin and/or polyglycerin having a mean degree of polymerization of 2 to 10.

Specific examples of these compounds may include glycerin, diglycerin, triglycerin, tetraglycerin, hexaglycerin and decaglycerin. These compounds may be used either singly or in combinations of two or more.

The fatty acid to be used as the raw material of the ester compound to be formulated in the present invention is a monobasic acid and dibasic acid. The monobasic acid must be straight-chain saturated fatty acid having 2 to 28 carbon atoms and is preferably straight-chain saturated fatty acid having 16 to 24 carbon atoms.

Specific examples of the monobasic acid may include acetic acid, propionic acid, caproic acid, caprylic acid, capric acid, lauric acid, myristic acid, palmitic acid, stearic acid, 10-hydroxystearic acid, 10-ketostearic acid, 12-hydroxystearic acid, arachic acid, behenic acid and montanic acid. These acids may be used either singly or in combinations of two or more.

Also, the dibasic acid must be aliphatic saturated dibasic acid having 12 to 28 carbon atoms and is preferably an aliphatic saturated dibasic acid having 16 to 24 carbon atoms.

Specific examples of the dibasic acid may include dodecanoic diacid, tetradecanoic diacid, eicosanic diacid, docosacosanoic diacid, tetracosanoic diacid, hexacosanoic diacid and octacosanoic diacid. These dibasic acids may be used either singly or in combinations of two or more.

As the raw material of the ester compound, the aforementioned glycerin or its condensate, straight-chain saturated fatty acid having 2 to 28 carbon atoms and aliphatic saturated dibasic acid having 12 to 28 carbon atoms may be used in an appropriate combination of these compounds. The ester compound may be produced by a known ester production method.

Among these combinations, a particularly preferable combination is glycerin, behenic acid and eicosanic diacid. An ester compound produced from these compounds further improves the dispersion stability of the ultraviolet protective preparation and handling characteristics and has no adverse influence on the storage stability of a cosmetic in which the ultraviolet protective preparation is formulated. This ester compound is available as a commercial product under the name of NOMCORT HK-G (trade name) from Nisshin OilliO Corp. Ltd.

The amount of the ester compound to be formulated in the present invention is 0.1 to 10% by weight, more preferably 0.2 to 3% by weight and even more preferably 0.4 to 2% by weight in the ultraviolet protective preparation. When the amount of the ester compound is less than 0.1% by weight, the ultraviolet protective powder cannot be dispersed stably. Also, when the amount of the ester compound exceeds 10% by weight, the viscosity of the ultraviolet protective preparation is increased, the handling characteristics are deteriorated and the spread of a cosmetic to be formulated become difficult.

(Ester Oil)

The ester oil to be formulated in the present invention is an oil agent which has a liquid or paste form at normal temperature and is produced from a carboxylic acid having a monovalent to hexavalent carboxyl group and 2 to 36 carbon atoms and an alcohol having a monohydric to hexahydric hydroxyl group and 1 to 36 carbon atoms. The ester oil is preferably an oil agent produced from a carboxylic acid having a monovalent to hexavalent carboxyl group and 2 to 28 carbon atoms and an alcohol having a monohydric to hexahydric hydroxyl group and 1 to 28 carbon atoms. Also, the total number of carbons of the ester oil is preferably 4 or more. The ester oil may be produced by a known ester production method.

Examples of the ester oil to be formulated in the present invention include isononyl isononanoate, isotridecyl isononanoate, isocetyl isostearate, isopropyl palmitate, 2-ethylhexyl palmitate, isooctyl palmitate, 2-ethylhexyldecyl palmitate, 2-heptylundecyl palmitate, isostearyl myristate, cetyl 2-ethylhexanoate, isocetyl stearate, butylstearate, oleyl oleate, octyldodecyl oleate, phytosteryl oleate, cholesteryl hydroxystearate, di-2-ethylhexylsuccinate, diisostearylmalate, diisobutyl adipate, 2-hexyldecyl adipate, diheptylundecyl adipate, diisopropyl cebacate, di-2-ethylhexyl cebacate, neopentyl glycol di-2-ethylhexanoate, neopentyl glycol dicaprate, caprylic/capric triglyceride, glyceryl tri-2-ethylhexanoate, glyceryl triisooctanoate, glyceryl triisostearater trimethylolpropane tri-2-ethylhexanoate, trimethylolpropane triusononanate, trimethylolpropane trilsostearate, pentaerythritol tetra-2-ethylhexanoate, diglyceryl tetraoctylate, diglyceryl tetraisostearate, dipentaerythritol hexaoctylate, dipentaerythritol hexaisononanate and dipentaerythritol hexaisostearate. One or two or more types selected from these compounds are combined upon use.

The ester oil in the present invention is preferably reduced in the amount of an unreacted carboxyl group or hydroxyl group therein. Therefore, it is more preferable that the acid value of the ester oil is 3 or less or the hydroxyl value of the ester oil is 5 or less. Moreover, it is even more preferable that both the amounts of a carboxyl group and a hydroxyl group in the ester oil are small. It is even more preferable that the ester oil has an acid value of 3 or less and a hydroxyl value of 5 or less.

The viscosity of the ester oil in the present invention is preferably 4 to 100 mPa·s, more preferably 5 to 80 mPa·s and even more preferably 15 to 70 mPa·s. The viscosity so-called here is a value measured by a Brookfield rotational viscometer and measured by a BL type viscometer manufactured by Toki Sangyo Co., Ltd. or the like.

Examples of the ester oil having a viscosity of 4 to 100 mPa·s at 20° C. include isononyl isononanoate (trade name: SALACOS 99, manufactured by Nisshin OilliO Corp. Ltd., viscosity: 9 mPa·s), isotridecyl isononanate (trade name: SALACOS 913, manufactured by Nisshin OilliO Corp. Ltd., viscosity: 11 mPa·s), isooctylpalmitate (trade name: SALACOS P-8, manufactured by Nisshin Oillio Corp. Ltd., viscosity: 11 mPa·s), cetyl 2-ethylhexanoate (trade name: EXEPARL HO, manufactured by Kao Corporation, viscosity: 14 mPa·s), neopentyl glycol di-2-ethylhexanoate (trade name: COSMOL 525, manufactured by Nisshin OilliO Corp. Ltd., viscosity: 12 mPa·s), neopentyl glycol dicaprate (trade name: Estemol N-01, manufactured by Nisshin OilliO Corp. Ltd., viscosity: 19 mPa·s), caprylic/capric triglyceride (trade name: O.D.O, manufactured by Nisshin Oillio Corp. Ltd., viscosity: 23 mPa·s) glyceryl tri-2-ethylhexanoate (trade name: T.I.O, manufactured by Nisshin OilliO Corp. Ltd., viscosity: 44 mPa·s), pentaerythritol tetra-2-ethylhexanoate (trade name: SALACOS 5408, manufactured by Nisshin Oillio Corp. Ltd., viscosity: 66 mPa·s), isostearyl myristate (trade name. Cosmol 812, manufactured by Nisshin OilliO Corp. Ltd., viscosity: 44 mPa·s) and di-2-heptylundecyl adipate (trade name: SALACOS 618, manufactured by Nisshin OilliO Corp. Ltd., viscosity: 66 mPa·s). Each viscosity is the value measured in one lot of each product.

Only one of these ester oils having a viscosity of 4 to 100 mPa·s may be used or two or more of these ester oils may be combined upon use. Also, if two or more of these ester oils having a viscosity out of the range from 4 to 100 mPa·s are combined, or the ester oil having a viscosity of 4 to 100 mPa·s is combined with the ester oil having a viscosity out of the range from 4 to 100 mPa·s, to prepare an ester oil having a viscosity of 4 to 100 mPa·s, the obtained ester oil may be used in the present invention. An ultraviolet protective preparation improved in handling characteristics and dispersion stability can be obtained by using an ester oil having a viscosity falling in such a range.

When one or two or more esters prepared from one or two or more polyols selected from neopentyl glycol, 2-methyl-2-ethyl-1,3-propanediol, glycerin, trimethylolpropane, diglycerin, ditrimethylolpropane, erythritol and pentaerythritol and one or two or more saturated straight-chain carboxylic acids having a monovalent carboxyl group and/or saturated branched carboxylic acids having a monovalent carboxyl group are used, this is preferable because this improves the handling characteristics and the dispersion stability of ultraviolet protective preparation more greatly.

Specific examples of the ester include neopentyl glycol di-2-ethylhexanoate, neopentyl glycol dicaprate, glyceryl tri (caprylate or caprate), glyceryl tri-2-ethylhexanoate, trimethylolpropane tri-2-ethylhexanoate and pentaerythritol tetra-2-ethylhexancate.

It is even more preferable to use one or two or more ester oils selected from neopentyl glycol dicaprate, glyceryl tri-2-ethylhexanoate and pentaerythritol tetra-2-ethylhexanoate because not only the handling characteristics and the dispersion stability of the ultraviolet protective preparation are improved but also excellent heat stability and oxidation stability are obtained.

The amount of the ester oil to be formulated in the present invention is preferably 39.9 to 89.9% by weight, more preferably 52 to 79.9% by weight and even more preferably 57.1 to 74.89 by weight in the ultraviolet protective preparation. When the amount of the ester oil is less than 39.9% by weight, the viscosity of the ultraviolet protective preparation increases, bringing about interior handling characteristics, whereas when the amount of the ester exceeds 89.9% by weight, the amount of the ultraviolet protective powder to be formulated is unsatisfied.

Hydrocarbon oil and silicone oil are known as the dispersion medium of the ultraviolet protective powder. When the ester oil in the present invention is compared with these oils, the ester oil is superior in functions when compounded in a cosmetic and has higher compatibility with the above ester compound. Particularly, the ester oil is superior in that it exhibits more excellent properties than hydrocarbon oil or silicone oil when it is compounded in a specified amount.

(Ultraviolet Protective Powder)

The ultraviolet protective powder used in the present invention has the effect of decreasing or preventing ultraviolet rays from reaching the skin and the like by shielding or diffusing ultraviolet rays when it is compounded in cosmetics. Any powder may be used as long as it can shield or diffuse ultraviolet rays. The ultraviolet protective powder is preferably a powder having a high ultraviolet diffusing effect and particularly preferably an ultraviolet diffusing powder constituted of an inorganic pigment.

Specifically, titanium dioxide, iron-containing titanium dioxide, zinc oxide, zirconium dioxide, iron oxide, aluminum oxide, cerium oxide, iron hydroxide, aluminum powder, silicon carbide and kaolin are preferable. Among these compounds, titanium dioxide, iron-containing titanium dioxide and zinc oxide are preferable. Particularly, when the maximum particle diameter of the compound is 100 nm or less, visible light is not diffused and therefore, it has high transparency and also high ultraviolet shielding effect. Therefore microparticle titanium dioxide, iron-containing microparticle titanium dioxide or zinc oxide having a particle diameter of 5 to 100 nm is more preferable.

One or two or more types among these compounds may be combined prior to use as the ultraviolet diffusing powder.

Among the above compounds, those which have been subjected to various surface treatments are preferable because not only they are improved in dispersibility in the ester oil but also they prevents optical activation and catalytic activation which are the cause of a deterioration of the ultraviolet protective preparation to be compounded or a cosmetic.

Examples of the surface treatment include conventionally known surface treatments, for example, silicone (for example, methylpolysiloxane, dimethylpolysiloxane or methylhydrogenpolysiloxane) treatment, silicone resin treatment, fluorine compound treatment, pendant treatment, silane coupling agent treatment, titanium coupling agent treatment, silane (alkylsilane) treatment, oil agent (for example, ester oil) treatment, N-acylated amino acid (for example, N-acylated glycine, N-acylated lysine and N-acylated glutamic acid and their salts) treatment, polyacrylic acid treatment, lecithin (hydrogenated soybean lecithin, hydrogenated egg yolk lecithin and their salts) treatment, metal soap (for example, aluminum stearate, zinc stearate and iron stearate) treatment, fatty acid (for example, stearic acid) treatment, metal oxide (for example, alumina and zirconia) treatment, metal hydroxide (for example, aluminum hydroxide) treatment, silica treatment and further, combined treatments which are combinations of two or more of these treatments).

Examples of a surface-treated ultraviolet protective preparation include zinc oxide which is surface-treated using methylpolysiloxane (trade name: MZ-303S and MZ-505S manufactured by Tayca Corporation), zinc oxide which is surface-treated using dimethylpolysiloxane (trade name: MZ-303M and MZ-505M manufactured by Tayca Corporation), microparticle titanium dioxide which is surface-treated using aluminum stearate (trade name: MT-100 and MT-100TV and MT-100Z manufactured by Tayca Corporation), titanium dioxide which is surface-treated using alumina (trade name: MT-500H manufactured by Tayca Corporation), titanium dioxide which is surface-treated using alumina, silica and silicone (trade name: MT-100ASA and SMT-100SAS manufactured by Tayca Corporation), titanium dioxide which is surface-treated using stearic acid and methylpolysiloxane (trade name: SA-TTO-S-4 manufactured by Miyoshi Kasei Corp.), iron-containing titanium dioxide which is surface-treated using methylpolysiloxane (trade name: SA-TTO-F-2 manufactured by Miyoshi Kasei Corp.), zinc oxide which is surface-treated using methylpolysiloxane and methylhydrogenpolysiloxane (trade name: SAS-UFZO-450 manufactured by Miyoshi Kasei Corp.) and titanium dioxide which is surface-treated using alumina, zirconia and stearic acid (trade name: TTO-S-2 manufactured by Ishihara Techno Corp.).

The ultraviolet protective powder to be formulated in the present invention is formulated in an amount range, preferably, from 10 to 50% by weight in the ultraviolet protective preparation. The amount of the ultraviolet protective powder to be formulated in the ultraviolet protective preparation is more preferably 15 to 45% by weight and even more preferably 24.8 to 39.9% by weight. When the amount is less than 10% by weight, it is necessary to extremely increase the amount of the ultraviolet protective to be formulated and also such a excessively low concentration brings about the case where the ultraviolet protective powder cannot be formulated in a required amount. When the amount of the ultraviolet protective preparation exceeds 50% by weight, the viscosity of the ultraviolet protective preparation is increased, leading to deteriorate the handling characteristics.

(Dispersant)

A dispersant may be formulated to further improve the dispersibility of the ultraviolet protective powder in the ultraviolet protective preparation. As the dispersant, a surfactant is primarily used. However, this surfactant is also cause of reduced water resistance in a W/O type cosmetic. Therefore, the dispersant to be compounded is preferably lecithin.

The lecithin so-called here indicates not only phosphatidyl choline but also mixed lipids including acyl glyceride type phospholipid. Examples of the form of lecithin include a paste form, gum form, powder form and granular form. Examples of the acyl glyceride type phospholipid include phosphatidyl choline, phosphatidyl ethanolamine, phosphatidyl inositol, phosphatidyl serine and phosphatidic acid. Examples of the acyl glyceride type phospholipid also include the so-called lysolecithins such as those obtained by hydrolyzing monoacyl glyceride type phosphatidyl choline, monoacyl glyceride type phosphatidyl ethanolamine, monoacyl glyceride type phosphatidyl inositol, monoacyl glyceride type phosphatidyl serine and monoacyl glyceride type phosphatidic acid by enzymatic treatment and a chemical reaction.

As the lecithin used in the present invention, various lecithins such as natural lecithin, lecithin obtained by treating or decomposing the natural lecithin enzymatically, hydrogenated lecithin and synthetic lecithin may be used. Examples of the natural lecithin include lecithins derived from a soybean, rapeseed, corn, cottonseed, peanut, linseed, sesame, safflower, olive, sunflower, rice, grape, avocado, coconut, egg yolk and cow brain. Also, these natural lecithins are subjected to enzymatic treatment or chemical treatment to run an ester exchange reaction, thereby producing lecithins in which the composition of structural fatty acids insoluble in acetone is regulated may be used. Among these lecithins, hydrogenated lecithin is highly stable in the preparation of the present invention and is therefore preferable.

The amount of the lecithin to be formulated in the ultraviolet protective preparation of the present invention is preferably 0.0001 to 0.05, more preferably 0.003 to 0.03 and even more preferably 0.005 to 0.02 to the total amount when the total amount of the above ester compound, ester oil and ultraviolet protective powder is 1. When the compounding ratio is less than 0.0001, the effect of the dispersant cannot be expected whereas when the ratio exceeds 0.05, there is the case where the water resistance and emulsification of a cosmetic are adversely affected.

(Other Additives)

The following components that are usually formulated in cosmetics may be added to the ultraviolet protective preparation of the present invention according to the need to the extent that the effect of the present invention is not impaired.

Examples of powder components include color pigments such as carbon black, chromium oxide, titanium-titanium dioxide sinter, tar dye, β-carotene, carthamin, carmine, chlorophyll, red iron oxide, yellow iron oxide, black iron oxide, Ultramarine blue and Prussian blue, white extender powders such as talc, silicone treated talc, sericite, calcium carbonate, silicic acid anhydride, barium sulfate, white mica, bentonite, smectites, magnesium oxide, diatomaceous earth, calcium silicate, barium silicate, magnesium silicate, magnesium carbonate, hydroxyapatite and boron nitride, mica coated with titanium dioxide, iron oxide-mica-titanium, silicone treated mica titanium, scaly foil, bismuth ox chloride, powders of organic high-molecular resins such as a polyethylene type resin, fluorine type resin, cellulose type resin and silicon resin, powders of organic low molecular compounds such as zinc stearate and N-acyllysine, natural organic powders such as a starch powder, silk powder and cellulose powder, powders of organic pigments such as Red No. 201, Red No. 202, Orange No. 203, Orange No. 204, Blue No. 404 and Yellow No. 401, organic powder pigments, for example, zirconium, barium or aluminum lakes such as Red No. 3, Red No. 104, Red No. 106, Orange No. 205, Yellow No, 4, Yellow No. 5, Green No. 3 and Blue No. 1, mica, metal powders such as a gold powder and combined powders such as titanium mica coated with micropowdery titanium dioxide.

Examples of the antioxidants include vitamin Cs, their derivatives and salts of these compounds, vitamin Es, their derivatives and salts of these compounds, BHT, BHA and gallic acid.

Examples of the sequestering agent include a Na salt of EDTA, phosphoric acid, citric acid, ascorbic acid, succinic acid, gluconic acid, sodium polyphosphate and sodium methaphosphate.

Examples of the antibacterial/antiseptic agent include p-hydroxybenzoic acid esters, phenoxy ethanol, benzoic acid, benzoate and salicylic acid.

Examples of the ultraviolet absorber include benzophenones, paraaminobenzoates, cinnamic acid esters, salicylates, dibenzoylmethanes and benzotriazoles.

Examples of the surfactant include soaps of higher fatty acids, alkyl sulfuric ester salt, polyoxyethylene alkyl ether sulfate, acyl-N-methyl taurate, alkyl ether phosphate esters, N-acyl aminate, alkyltrimethylammonium chloride, dialkyldimethylammonium chloride, benzalkonium chloride, alktylamidodimethylaminoacetic acid betaine, 2-alkyl-N-carboxy-N-hydroxyimidazolinium betaine, glycerin fatty acid esters, polyglycerin fatty acid esters, sorbitan fatty acid esters, propylene glycol esters, polyoxyethylene sorbitan fatty acid esters, polyoxyethylene fatty acid esters, polyoxyethylene alkyl ethers, hydrogenated castor oil derivatives, dextrin fatty acid esters, glycerin alkyl ethers and sucrose fatty acid esters.

Examples of the oily raw material include avocado oil, linseed oil, almond oil, olive oil, camellia oil, macadenia nut oil, rapeseed oil, beef tallow, beef foot tallow, beef born tallow, hydrogenated beef tallow, wheat embryo oil, sesame oil, rice embryo oil, rice bran oil, safflower oil, soybean oil, evening primrose oil, corn oil, horse tallow, palm oil, palm kernel oil, castor oil, hydrogenated castor oil, sunflower oil, jojoba oil, beeswax, mink oil, cotton seed oil, coconut oil, hydrogenated coconut oil, peanut oil, lanolin, liquid lanolin, hydrogenated lanolin, reduced lanolin, lanolin fatty acid isopropyl carnauba wax, candelilla wax, beeswax, liquid paraffin, paraffin, waseline, ceresin, microcrystalline wax, squalane, squalene, ceresin, paraffin wax, α-olefin oligomer, ether oils, silicone oil and cyclic silicone oil.

Examples of the higher fatty acid include lauric acid, myristic acid, palmitic acid, stearic acid, isostearic acid, behenic acid, undecylenic acid, oleic acid, linoleic acid, linolenic acid and 12-hydroxystearic acid. Examples of the saturated straight-chain alcohol include cetanol, stearyl alcohol, isostearyl alcohol, behenyl alcohol and 2-octyldodecanol. Examples of the straight-chain monoalkyl glyceryl ether include monocetyl glyceryl ether (chimyl alcohol), monostearyl glyceryl ether (bathyl alcohol) and monobehenyl glyceryl ether.

In addition, examples of the humectant include propylene glycol, isoprene glycol, 1,2-pentanediol, 1,3-butylene glycol, dipropylene glycol, hexanediol, polyethylene glycol, glycerin, diglycerin, triglycerin, polyglycerin, neopentyl glycol, sorbitol, erythritol, pentaerythritol, glucose, galactose, fructose, sucrose, maltose, xylose, xylobiose, reduced product of oligosaccharide, protein, mucopolysaccharide, collagen, elastin, keratin, triethanolamine, sodium lactate and sodium pyrrolidonecarboxylate. Examples of cosmetic components may include vitamins, their derivatives and salts of these compounds, antiphlogistics and crude drugs. Examples of the pH regulator may include edetic acid, disodium edetate, sodium chloride, citric acid, sodium citrate, sodium hydroxide, potassium hydroxide and triethanolamine.

(Material Characteristics of the Ultraviolet Protective Preparation)

The ultraviolet protective preparation of the present invention is further improved in handling characteristics and the dispersion stability thereof by allowing the dynamic viscoelasticity and thixotropy to fall in each given range. The content of the ester compound in the ultraviolet protective preparation is adjusted to a value falling in the more preferable range or even more preferable range explained above and, as the esteroil, one having a viscosity of 4 to 100 mPa·s is used, whereby the dynamic viscoelasticity and thixotropy can be fallen in each desirable range.

As to the specific ranges of the dynamic viscoelasticity (storage elastic modulus and loss elastic modulus), it is preferable that the storage elastic modulus (G') when a shear stress (τ) of 0.1 to 10 Pa is applied at a frequency of 1 Hz at 25° C. be 10 to 5000 Pa and the loss elastic modulus (G") when a shear stress (τ) of 0.1 to 10 Pa is applied at a frequency of 1 Hz be 80 to 3000 Pa. It is more preferable that the storage elastic modulus (G') is 50 to 2000 Pa and the loss elastic modulus (G") is 90 to 1500 Pa. It is even more preferable that the storage elastic modulus (G') is 100 to 1500 Pa and the loss elastic modulus (G") is 100 to 1200 Pa.

Here, the storage elastic modulus is a value indicating elasticity and the loss elastic modulus is a value indicating viscosity. The ultraviolet protective preparation exhibits moderate elasticity and viscosity and has excellent dispersion stability and handling characteristics when the storage elastic modulus and the loss elastic modulus fall in such ranges. When the storage elastic modulus is 10 Pa or more and the loss elastic modulus is 80 Pa or more, the dispersion stability of the ultraviolet protective preparation is further improved. When the storage elastic modulus is 5000 Pa or less and the loss elastic modulus is 3000 Pa or less, the handling characteristics are further improved because the ultraviolet protective preparation exhibits no solid gummy or clay-like nature.

Also, the area enclosed by the shear rate and shear stress measured at 25° C. in a hysteresis loop, which is an index exhibiting thixotropy, is preferably 300 to 3000 Pa×1/s. The area is more preferably 400 to 2000 Pa×1/s.

Materials exhibiting thixotropy has such a nature that it is changed to a liquid from a solid (semisolid) by applying force. This nature that these materials have ensures that they keep a solid to semisolid stable state when stored (in unforced state) and are fluidized by applying force to a certain extent, which makes easy to handle these materials when they are weighed and transported. When the above area is 300 Pa×1/s or more, the necessary thixotropy is secured and the dispersion stability is further improved. When the above area is 3000 Pa×1/s or less, large force becomes unnecessary when the ultraviolet protective preparation is changed to a fluid from a solid or semisolid, which further improves the handling characteristics and also, is increased in the rate of restoration from a liquid state to a solid or semisolid state and therefore, the dispersion stability is further improved.

The hysteresis loop that is an index exhibiting the dynamic viscoelasticity and thixotropy may be measured using a stress control type rheometer (for example, Rheostress RS1, manufactured by HAAKE Company).

(Method of Producing the Ultraviolet Protective Preparation)

Although no particular limitation is imposed on the method of producing the ultraviolet protective preparation of the present invention, the ultraviolet protective preparation may be produced, for example, by dissolving and mixing the ester compound (and lecithin) in the ester oil, then adding the ultraviolet protective powder and then mixing these components to carry out dispersing treatment. The dispersing treatment may be carried out by using a dispersing apparatus such as a homomixer, roll mill, ball mill, basket mill, vertical type beads mill, horizontal type beads mill, beads mill with a pin, colloid mill, attritor, high-pressure homogenizer, dyno mill, microfluidizer and ultrasonic dispersing machine so as to make the mixture uniform. Though no particular limitation is imposed on the dispersing treatment temperature and time, for example, the treating temperature is preferably in a range from −5° C. to 120° C. and the dispersing treatment time is preferably in a range from 1 minute to 2 hours. Treatments such as deaerating treatment and filtering treatment may be further carried out according to the need after the dispersing treatment.

(Cosmetics)

The ultraviolet protective preparation of the present invention may be formulated in cosmetics. No particular limitation is imposed on the use and preparation form of the cosmetics insofar as these cosmetics need to be formulated with an ultraviolet diffusing agent. Examples of these cosmetics include skin lotions, milky lotions, creams, ointments, foundations, lip creams, lipsticks, mascaras, eye shadows, eyebrows, nail enamels and cheek colors. The ultraviolet protective preparation is formulated in a cosmetic in an amount of 3 to 95% by weight. The amount of the ultraviolet protective preparation obtained in the present invention is more preferably 5 to 92% by weight and even more preferably 10 to 90% by weight.

The ultraviolet protective preparation is highly dispersible in cosmetics formulated therewith and does not adversely affect an emulsion. Also, the ultraviolet protective preparation of the present invention does not adversely affect the function and storage stability of cosmetics formulated therewith.

The present invention will be explained below in more detail by way of examples, which, however, are not intended to be limiting of the present invention.

The dynamic viscoelasticity and the thixotropy may be measured using a stress control type rheometer: Rheostress RS1 (manufactured by HAAKE Company).

(1) Dynamic viscoelasticity (storage elastic modulus/loss elastic modulus)

The storage elastic modulus (G') and the loss elastic modulus (G") were measured in the following condition: measuring temperature: 25° C., frequency: 1 Hz, shear force: changed between 0.1 and 10 Pa. As the sensor, a plate/cone having a diameter of 3.5 cm was used.

(2) Thyrotrophic characteristics

A sample was measured at a temperature of 25° C. at a shear rate changed continuously from 0.01 to 100 (1/s) for 10 minutes, then kept at a shear rate of 100 (1/s) for 30 seconds and further at a shear rate changed continuously from 100 to 0.01 (1/s), to detect the area within the drawn flow curve. As the sensor, a plate/cone having a diameter of 3.5 cm was used.

For the confirmation of the dispersibility of the ultraviolet protective preparation in a cosmetic when the ultraviolet protective preparation was added in the cosmetic, the dispersibility of the ultraviolet protective preparation in an oil agents (squalling or cyclic silicone oil) frequently used in the ordinary cosmetics was confirmed. 10 g of a sample and 90 g of squalane or cyclic silicone were weighed and placed in a beaker and the mixture was dispersed by a disper rotated at 1000 rpm for 5 minutes while heating to 60° C. Then, the dispersion was transferred to a test tube and was visually observed to confirm the state of the dispersion. As a result, the state of the dispersion was rated as follows: the case where an ultraviolet protective powder was uniformly dispersed was rated as ○, the case where an ultraviolet protective powder was slightly coagulated and sedimented was rated as Δ and the case where an ultraviolet protective powder was considerably coagulated and sedimented was rated as x.

Also, the dispersion stability of the ultraviolet protective preparation of the present invention was evaluated in the following manner.

The method of evaluation is as follows.

80 g of each sample was placed in a 100 ml lidded transparent glass bottle, which was then allowed to stand in a thermostatic chamber set to each temperature and the sample was evaluated in the following condition.

(1) Short Term Dispersion Stability

The sample was allowed to stand at 25° C. for 24 hours after produced, to confirm whether or not oil separation and the sedimentation of an ultraviolet protective powder were observed. As a result, the case where the dispersion was stable was rated as ◎, the case where sedimentation of an ultraviolet protective powder and oil separation were slightly observed was rated as ○, the case where sedimentation of an ultraviolet protective powder and oil separation were somewhat observed was rated as Δ and the case where sedimentation of an ultraviolet protective powder and oil separation were considerably observed was rated as x.

(2) High-Temperature Dispersion Stability

After each sample was allowed to stand at 50° C. for one month, it was confirmed whether or not oil separation and the sedimentation of an ultraviolet protective powder were observed. As a result, the case where the dispersion was stable was rated as ◎, the case where sedimentation of an ultraviolet protective powder and oil separation were slightly observed was rated as ○, the case where sedimentation of an ultraviolet protective powder and oil separation were somewhat observed was rated as Δ and the case where sedimentation of an ultraviolet protective powder and oil separation were considerably observed was rated as x.

(3) Low-Temperature Dispersion Stability

After each sample was allowed to stand at 5° C. for six months, it was confirmed whether or not oil separation and the sedimentation of an ultraviolet protective powder were observed. As a result, the case where the dispersion was stable was rated as ⊚, the case where sedimentation of an ultraviolet protective powder and oil separation were slightly observed was rated as ○, the case where sedimentation of an ultraviolet protective powder and oil separation were somewhat observed was rated as Δ and the case where sedimentation of an ultraviolet protective powder and oil separation were considerably observed was rated as x.

(4) Dispersion Stability Under Varied Temperatures

After each sample was stored for one month in the situation where the temperature of the sample was varied from −10° C. to 40° C. and vice versa every 24 hours, it was confirmed whether or not oil separation and the sedimentation of an ultraviolet protective powder were observed. As a result, the case where the dispersion was stable was rated as ⊚, the case where sedimentation of an ultraviolet protective powder and oil separation were slightly observed was rated as ○, the case where sedimentation of an ultraviolet protective powder and oil separation were somewhat observed was rated as Δ and the case where sedimentation of an ultraviolet protective powder and oil separation were considerably observed was rated as x.

Example 1

90 g of an ester compound (trade name: NOMCORT HK-G, manufactured by Nisshin OilliO Corp. Ltd., the same as follows) prepared from glycerin, behenic acid and eicosanic diacid was added to 2310 g of glyceryl tri-2-ethylhexanoate (trade name: T.I.O, manufactured by Nisshin OilliO Corp. Ltd., viscosity: 44 mPa·s at 20° C., the same as follows) placed in a 2 l stainless stein and the mixture was heated to 70° C. to melt the mixture. 600 g of micro powdery titanium dioxide which was surface-treated using aluminum stearate (trade name: MT-100TV manufactured by Tayca Corporation, mean value primary particle diameter: 15 nm, the same as follows) was gradually added to the mixture to premix the resulting mixture at 5000 rpm for 15 minutes by using a homomixer (trade name: Quick Homomixer, manufactured by Mizuho Industrial Co., Ltd., the same as follows). The obtained pre-mixture was subjected to two-pass treatment using a high-pressure homogenizer (product name:homogenizer, Sanwa Machine CO. INC.) under 300 MPa to obtain 1500 g of an ultraviolet protective preparation according to the present invention.

Example 2

The same procedures as in Example 1 were conducted except for the formulation of the raw material was changed to 18 g of an ester compound (NOMCORT HK-G) prepared from glycerin, behenic acid and eicosanic diacid, 1932 g of glyceryl tri-2-ethylhexanoate (T.I.O) and 1050 g of micropowdery titanium dioxide which was surface-treated with aluminum stearate (MT-100 TV) to obtain 1500 g of an ultraviolet protective preparation according to the present invention.

Example 3

The same procedures as in Example 1 were conducted except for the raw material and its formulation were changed to 30 g of an ester compound (NOMCORT HK-G) prepared from glycerin, behenic acid and eicosanic diacid, 1920 g of neopentyl glycol dicaprate (trade name: Estemol N-01, manufactured by Nisshin OilliO Corp. Ltd., viscosity: 19 mPa·s at 20° C., the same as follows) and 1050 g of micropowdery titanium dioxide which was surface-treated with aluminum stearate (MT-100 TV) to obtain 1500 g of an ultraviolet protective preparation according to the present invention.

Example 4

The same procedures as in Example 1 were conducted except for the raw material and its formulation were changed to 18 g of an ester compound (NOMCORT HK-G) prepared from glycerin, behenic acid and eicosanic diacid, 1932 g of pentaerythritol tetra-2-ethylhexanoate (trade name: SALACOS 54081 manufactured by Nisshin Oillio Corp, Ltd., viscosity: 66 mPa·s at 20° C., the same as follows) and 1050 g of micro powdery titanium dioxide which was surface-treated with stearic acid and cyclopolysiloxane (trade name: SA-TTO-S-4, manufactured by Miyoshi Kasei Corp.), the dispersing machine was changed to a ball mill (trade name: HD Pot Mill, manufactured by Tokyo Glass Kikai Corp., Use Zirconia ball) from the high-pressure homogenizer and the treating time was changed to 40 minutes to obtain 2600 g of an ultraviolet protective preparation according to the present invention.

Example 5

18 g of an ester compound (NOMCORT HK-G) prepared from glycerin, behenic acid and eicosanic diacid and 30 g of hydrogenated high-purity lecithin (trade name: BASIS LP-20H, manufactured by Nisshin OilliO Corp. Ltd., the same as follows) were added to 1902 g of glyceryl tri-2-ethylhexanoate (T.I.O) placed in a 2 l stainless stein and the mixture was heated to 80° C. to melt the mixture. 1050 g of micro powdery titanium dioxide which was surface-treated using aluminum stearate (MT-100TV) was gradually added to the mixture to premix the resulting mixture at 5000 rpm for 15 minutes by using a homomixer. The obtained pre-mixture was subjected to two-pass treatment using a high-pressure homogenizer under 300 MPa to obtain 1500 g of an ultraviolet protective preparation according to the present invention.

Example 6

The same procedures as in Example 5 were conducted except for the raw material and its formulation were changed to 24 g of an ester compound (NOMCORT HK-G) prepared from glycerin, behenic acid and eicosanic diacid, 1812 g of neopentyl glycol dicaprate (trade name: Estemol N-01), 1140 g of micropowdery titanium dioxide which was surface-treated with aluminum stearate (MT-100 TV) and 24 g of hydrogenated high-purity lecithin (BASIS LP-20H) to obtain 1500 g of an ultraviolet protective preparation according to the present invention.

Example 7

The same procedures as in Example 1 were conducted except for the raw material and its formulation were changed to 30 g of an ester compound (NOMCORT HK-G) prepared from glycerin, behenic acid and eicosanic diacid, 1860 g of glyceryl tri-2-ethylhexanoate (T.I.O) and 1110 g of micropowdery zinc dioxide which was surface-treated with methylpolysiloxane (trade name: MZ-303S, manufactured by Tayca Corporation, mean value particle diameter: 30-40 nm), to obtain 1500 g of an ultraviolet protective preparation according to the present invention.

Example 8

The same procedures as in Example 1 were conducted except for the raw material and its formulation were changed to 18 g of an ester compound (NOMCORT HK-G) prepared from glycerin, behenic acid and eicosanic diacid, 1632 g of glyceryl tri-2-ethylhexanoate (T.I.O) and 1350 g of micropowdery zinc oxide which was surface-treated with methylpolysiloxane (trade name: MZ-505S, manufactured by Tayca Corporation, mean value particle diameter: 20-30 nm), to obtain 1500 g of an ultraviolet protective preparation according to the present invention.

Example 9

The same procedures as in Example 1 were conducted except for the raw material and its formulation were changed to 24 g of an ester compound (NOMCORT HK-G) prepared from glycerin, behenic acid and eicosanic diacid, 1866 g of glyceryl tri-2-ethylhexanoate (T.I.O), 600 g of micropowdery titanium dioxide which was surface-treated with aluminum stearate (MT-100 TV) and 510 g of micropowdery zinc oxide which was surface-treated with methylpolysiloxane (MZ-505S) to obtain 1500 g of an ultraviolet protective preparation according to the present invention.

Example 10

The same procedures as in Example 1 were conducted except for the raw material and its formulation were changed to 24 g of an ester compound (NOMCORT HK-G) prepared from glycerin, behenic acid and eicosanic diacid, 1926 g of diisostearyl malate (trade name: COSMOL 222, manufactured by Nisshin OilliO Corp. Ltd., viscosity: 5500 mPa·s at 20° C.) and 1050 g of micropowdery titanium dioxide which was surface-treated with aluminum stearate (MT-100 TV), to obtain 1500 g of an ultraviolet protective preparation according to the present invention.

Example 11

30 g of an ester compound (NOMCORT HK-G) prepared from glycerin, behenic acid and eicosanic diacid was added to 1830 g of isooctyl palmitate (trade name: SALACOS P-8, manufactured by Nisshin OilliO Corp. Ltd., viscosity: 11 mPa·s at 20° C.) placed in a 2.1 stainless stein and the mixture was heated to 70° C. to melt the mixture. 1140 g of micropowdery titanium dioxide which was surface-treated using aluminum stearate (MT-100TV) was gradually added to the mixture to treat the resulting mixture by using a homomixer at 8000 rpm for 30 minutes, to obtain 1500 g of an ultraviolet protective preparation according to the present invention.

Comparative Example 1

The same procedures as in Example 1 were conducted except for the formulation of the raw material were changed to 1.5 g of an ester compound (NOMCORT HK-G) prepared from glycerin, behenic acid and eicosanic diacid, 1948.5 g of glyceryl tri-2-ethylhexanoate (T.I.O) and 1050 g of micropowdery titanium dioxide which was surface-treated with aluminum stearate (MT-100 TV), to obtain 1500 g of an ultraviolet protective preparation.

Comparative Example 2

360 g of an ester compound (NOMCORT HK-G) prepared from glycerin, behenic acid and eicosanic diacid was added to 2340 g of glyceryl tri-2-ethylhexanoate (T.I.O) placed in a 2 l stainless stein and the mixture was heated to 70° C. to melt the mixture. 300 g of micropowdery titanium dioxide, which was surface-treated using aluminum stearate (MT-100TV), was gradually added to the mixture to premix the resulting mixture by using a homomixer at 5000 rpm for 15 minutes. The resulting pre-mixture was treated with a three-roll mill (trade name: EXAKT, manufactured by Corp. Nagase Screen Insatsu Kenkyusho), to obtain 2700 g of an ultraviolet protective preparation.

Comparative Example 3

The same procedures as in Example 1 were conducted except for the raw material and its formulation were changed to 24 g of an ester compound (NOMCORT HK-G) prepared from glycerine behenic acid and eicosanic diacid, 1926 g of squalane (trade name: Sophimsqualane S, manufactured by Iwase Cosfa Co., Ltd., viscosity: 32 Pa·s at 20° C.) and 1050 g of micropowdery titanium dioxide which was surface-treated with aluminum stearate (MT-100 TV), to obtain 1500 g of an ultraviolet protective preparation.

Comparative Example 4

The same procedures as in Example 1 were conducted except for the formulation of the raw material was changed to 6 g of an ester compound (NOMCORT HK-G) prepared from glycerin, behenic acid and eicosanic diacid, 1344 g of glyceryl tri-2-ethylhexanoate (T.I.O) and 1650 g of micropowdery titanium dioxide which was surface-treated with aluminum stearate (MT-100 TV), to obtain 1500 g of an ultraviolet protective preparation.

Comparative Example 5

The same procedures as in Example 1 were conducted except for the raw material and its formulation was changed to 90 g of dextrin palmitate (dispersant, trade name: Rheopearl TL, manufactured by Chiba Seifun Co., Ltd.), 1860 g of glyceryl tri-2-ethylhexanoate (T.I.O) and 1050 g of micropowdery titanium dioxide which was surface-treated with aluminum stearate (MT-100 TV), to obtain 1500 g of an ultraviolet protective preparation.

Comparative Example 6

The same procedures as in Example 1 were conducted except for the raw material and its formulation was changed to 300 g of polyhydroxystearic acid (dispersant, trade name: Arlacel P-100, manufactured by Uniqema Corp., the same as follows), 1650 g of glyceryl tri-2-ethylhexanoate (T.I.O) and 1050 g of micropowdery titanium dioxide which was surface-treated with aluminum stearate (MT-100 TV), to obtain 1500 g of an ultraviolet protective preparation.

Comparative Example 7

The same procedures as in Example 1 were conducted except for the raw material and its formulation was changed to 90 g of polyhydroxystearic acid (Arlacel P-100), 1650 g of glyceryl tri-2-ethylhexanoate (T.I.O) and 1260 g of micropowdery titanium dioxide which was surface-treated with aluminum stearate (MT-100 TV), to obtain 1500 g of an ultraviolet protective preparation.

Comparative Example 8

The same procedures as in Comparative Example 2 were conducted except for the raw material and its formulation were changed to 180 g of an ester compound (NOMCORT HK-G) prepared from glycerin, behenic acid and eicosanic diacid, 1140 g of neopentyl glycol dicaprate (ESTEMOL N-01) and 1680 g of micropowdery titanium dioxide which was surface-treated with aluminum stearate (MT-100 TV) and the pre-dispersion operating machine was changed to a disper mixer (Mizuho Industrial Co., Ltd.), to obtain 2600 g of an ultraviolet protective preparation.

Comparative Example 9

The same procedures as in Example 1 were conducted except for the formulation of the raw material were changed to 60 g of an ester compound (NOMCORT HK-G) prepared from glycerin, behenic acid and eicosanic diacid, 2670 g of glyceryl tri-2-ethylhexanoate (T.I.O) and 270 g of micropowdery titanium dioxide which was surface-treated with aluminum stearate (MT-100 TV), to obtain 1500 g of an ultraviolet protective preparation.

Comparative Example 10

The same procedures as in Example 1 were conducted except for the formulation of the raw material were changed to 60 g of an ester compound (NOMCORT HK-G) prepared from glycerin, behenic acid and eicosanic diacid, 2760 g of glyceryl tri-2-ethylhexanoate (T.I.O) and 180 g of micropowdery titanium dioxide which was surface-treated with aluminum stearate (MT-100 TV), to obtain 1500 g of an ultraviolet protective preparation.

Comparative Example 11

The same procedures as in Example 1 were conducted except for the raw material and its formulation were changed to 1.5 g of an ester compound (NOMCORT HK-G) prepared from glycerin, behenic acid and eicosanic diacid, 1948.5 g of glyceryl tri-2-ethylhexanoate and 1050 g of zinc oxide which was surface-treated with methylpolysiloxane (MT-505S), to obtain 1500 g of an ultraviolet protective preparation.

Each formulation of the ultraviolet protective preparations prepared in Examples 1 to 11 and Comparative Examples 1 to 11 is shown in Tables 1 and 2. Here, the numerals in the parenthesis described in the column of other components in Table 1 indicate the ratio of the amount by weight of lecithin to the total amount when the total amount of the above ester compound, ester oil and ultraviolet protective powder is 1.

TABLE 1

Table 1: Formulation of the ultraviolet protective preparation (wt %)

| | Ester compound | Ester oil | Ultraviolet protective powder | Other components | Total |
|---|---|---|---|---|---|
| Example 1 | 3.0 NOMCORT HK-G | 77.0 T.I.O | 20.0 MT-100TV | 0 | 100.0 |
| Example 2 | 0.6 NOMCORT HK-G | 64.4 T.I.O | 35.0 MT-100TV | 0 | 100.0 |
| Example 3 | 1.0 NOMCORT HK-G | 64.0 ESTEMOL N-01 | 35.0 MT-100TV | 0 | 100.0 |
| Example 4 | 0.6 NOMCORT HK-G | 64.4 SALACOS 5408 | 35.0 SA-TTO-S-4 | 0 | 100.0 |
| Example 5 | 0.6 NOMCORT HK-G | 63.4 T.I.O | 35.0 MT-100TV | 1.0 BASIS LP-20H (0.0101) | 100.0 |
| Example 6 | 0.8 NOMCORT HG-K | 60.4 ESTEMOL N-01 | 38.0 MT-100TV | 0.8 BASIS LP-20H (0.0081) | 100.0 |
| Example 7 | 1.0 NOMCORT HK-G | 62.0 T.I.O | 37.0 MZ-303S | 0 | 100.0 |
| Example 8 | 0.6 NOMCORT HK-G | 54.4 T.I.O | 45.0 MZ-505S | 0 | 100.0 |
| Example 9 | 0.8 NOMCORT HK-G | 62.2 T.I.O | 20.0 MT-100TV 17.0 MZ-505S | 0 | 100.0 |
| Example 10 | 0.8 NOMCORT HK-G | 64.2 COSMOL 222 | 35.0 MT-100TV | 0 | 100.0 |
| Example 11 | 1.0 NOMCORT HK-G | 61.0 SALACOSP-8 | 38.0 MT-100TV | 0 | 100.0 |

TABLE 2

Table 1: Formulation of the ultraviolet protective preparation (wt %)

| | Ester compound | Ester oil | Ultraviolet protective powder | Other components | Total |
|---|---|---|---|---|---|
| Comparative Example 1 | 0.05 NOMCORT HK-G | 64.95 T.I.O | 35.0 MT-100TV | 0 | 100.0 |
| Comparative Example 2 | 12.0 NOMCORT HK-G | 78.0 T.I.O | 10.0 MT-100TV | 0 | 100.0 |
| Comparative Example 3 | 0.8 NOMCORT HK-G | 0 | 35.0 MT-100TV | 64.2 SophimsqualaneS | 100.0 |
| Comparative Example 4 | 0.2 NOMCORT HK-G | 44.8 T.I.O | 55.0 MT-100TV | 0 | 100.0 |
| Comparative Example 5 | 0 | 62.0 T.I.O | 35.0 MT-100TV | 3.0 Lheopearl LT (Dispersant) | 100.0 |
| Comparative Example 6 | 0 | 55.0 T.I.O | 35.0 MT-100TV | 10.0 Arlacel P-100 (Dispersant) | 100.0 |
| Comparative Example 7 | 0 | 55.0 T.I.O | 42.0 MZ-100TV | 3.0 Arlacel P-100 (Dispersant) | 100.0 |
| Comparative Example 8 | 6.0 NOMCORT HK-G | 38.0 ESTEMOL N-01 | 56.0 MZ-100TV | 0 | 100.0 |
| Comparative Example 9 | 2.0 NOMCORT HK-G | 89.0 T.I.O | 9.0 MT-100TV | 0 | 100.0 |
| Comparative Example 10 | 2.0 NOMCORT HK-G | 92.0 T.I.O | 6.0 MT-100TV | 0 | 100.0 |
| Comparative Example 11 | 0.05 NOMCORT HK-G | 64.95 T.I.O | 35.0 MZ-505S | 0 | 100.0 |

The storage elastic modulus, loss elastic modulus and thixotropy of each of Examples 1 to 11 and Comparative Examples 1 to 11 are shown in Table 3.

TABLE 3

Table 3: Results of measurement of storage elastic modulus, loss elastic modulus and thixotropy

| | Storage elastic modulus (Pa) | Loss elastic modulus (Pa) | Thixotropy (Pa × 1/s) |
|---|---|---|---|
| Example 1 | 1600-4090 | 630-2740 | 2095 |
| Example 2 | 240-1965 | 325-770 | 615 |
| Example 3 | 125-340 | 235-265 | 440 |
| Example 4 | 1520-3760 | 640-1455 | 1751 |
| Example 5 | 50-765 | 130-510 | 1379 |
| Example 6 | 175-530 | 475-780 | 1410 |
| Example 7 | 480-1730 | 430-750 | 636 |
| Example 8 | 160-1500 | 220-590 | 1057 |
| Example 9 | 70-730 | 135-280 | 927 |
| Example 10 | 3440-6380 | 645-2210 | 4424 |
| Example 11 | 43-49 | 125-200 | 562 |
| Comparative Example 1 | 1.5-180 | 8.5-180 | 310 |
| Comparative Example 2 | 7620-188800 | 26940-298400 | 55080 |
| Comparative Example 3 | 10-700 | 22-150 | 183 |
| Comparative Example 4 | 590-285500 | 26940-298400 | 68560 |
| Comparative Example 5 | 230-1300 | 200-335 | 254 |
| Comparative Example 6 | 0.1-0.5 | 1.5-2.5 | 179 |
| Comparative Example 7 | 0.1-0.5 | 2.0-2.5 | 125 |
| Comparative Example 8 | Unmeasurable* | Unmeasurable* | Unmeasurable* |
| Comparative Example 9 | 2-35 | 5.5-18 | 625 |
| Comparative Example 10 | 1-33 | 4-30 | 491 |
| Comparative Example 11 | 1-120 | 4-125 | 139 |

*Unmeasurable because the sample is very hard.

Next, The results of evaluation of the dispersibility of Examples 1 to 11 and Comparative Examples 1 to 11 in an oil agent and the storage stability of these examples are shown in Table 4.

TABLE 4

Table 4: The results of evaluation of the dispersibility and the storage stability.

| | Dispersibility in an oil agent (squalane) | Dispersibility in an oil agent (cyclic silicone) | Short-term dispersion stability | High-temperature dispersion stability (50° C.) | Low-temperature dispersion stability (5° C.) | Dispersion stability under varied temperatures (−10-40° C.) |
|---|---|---|---|---|---|---|
| Example 1 | ○ | ○ | ◎ | ◎ | ◎ | ◎ |
| Example 2 | ○ | ○ | ◎ | ◎ | ◎ | ◎ |
| Example 3 | ○ | ○ | ◎ | ○ | ◎ | ○ |
| Example 4 | ○ | ○ | ◎ | ◎ | ◎ | ◎ |
| Example 5 | ○ | ○ | ◎ | ◎ | ◎ | ◎ |
| Example 6 | ○ | ○ | ◎ | ◎ | ◎ | ◎ |
| Example 7 | ○ | ○ | ◎ | ◎ | ◎ | ◎ |
| Example 8 | ○ | ○ | ◎ | ◎ | ◎ | ◎ |
| Example 9 | ○ | ○ | ◎ | ○ | ◎ | ◎ |
| Example 10 | ○ | ○ | ◎ | ◎ | ◎ | ◎ |
| Example 11 | ○ | ○ | ◎ | ○ | ◎ | ○ |
| Comparative Example 1 | ○ | ○ | Δ | X | Δ | X |
| Comparative Example 2 | Δ | Δ | ◎ | Δ | Δ | Δ |
| Comparative Example 3 | ○ | ○ | ○ | Δ | Δ | Δ |
| Comparative Example 4 | Δ | Δ | ◎ | ○ | ○ | ○ |
| Comparative Example 5 | ○ | ○ | ◎ | Δ | ○ | Δ |
| Comparative Example 6 | ○ | X | ○ | X | X | X |
| Comparative Example 7 | ○ | X | ○ | X | X | X |
| Comparative Example 8 | Δ | Δ | ◎ | ○ | ◎ | ○ |
| Comparative Example 9 | ○ | ○ | ○ | Δ | Δ | Δ |
| Comparative Example 10 | ○ | ○ | ○ | Δ | Δ | Δ |
| Comparative Example 11 | ○ | ○ | Δ | X | Δ | X |

It is found from Tables 3 and 4 that the ultraviolet protective preparations of the present invention exhibit better qualities and have higher dispersibility and dispersion stability in an oil agent than those obtained in Comparative Examples.

Examples 12 to 22

Using each ultraviolet protective preparation produced in Examples 1 to 11, a W/O type non-chemical UV cream was prepared such that the amount of the ultraviolet protective preparation was 8% by weight to the total amount. Each formulation of these W/O type non-chemical UV creams is shown in Tables 5 to 7.

TABLE 5

Table 5: Formulation of the W/O type non-chemical UV cream unit: g
The numerals in the parenthesis indicate percentage composition unit: wt %

| | Example 12 | Example 13 | Example 14 | Example 15 |
|---|---|---|---|---|
| [Oil phase] | | | | |
| Volatile cyclic silicone | 8.6 | 40.0 | 40.0 | 40.0 |
| | (4.3) | (20.0) | (20.0) | (20.0) |
| Ultraviolet protective preparation | 80.0 | 45.8 | 45.8 | 45.8 |
| (8% by weight as an ultraviolet | (40.0) | (22.9) | (22.9) | (22.9) |
| protective powder) | Using Example 1 | Using Example 2 | Using Example 3 | Using Example 4 |

TABLE 5-continued

Table 5: Formulation of the W/O type non-chemical UV cream unit: g
The numerals in the parenthesis indicate percentage composition unit: wt %

|  | Example 12 | Example 13 | Example 14 | Example 15 |
|---|---|---|---|---|
| Squalane | 0 | 2.8 | 2.8 | 2.8 |
|  | (0) | (1.4) | (1.4) | (1.4) |
| Dimethyconchopolyol | 4.0 | 4.0 | 4.0 | 4.0 |
|  | (2.0) | (2.0) | (2.0) | (2.0) |
| Organic modified montmorillonite | 1.0 | 1.0 | 1.0 | 1.0 |
|  | (0.5) | (0.5) | (0.5) | (0.5) |
| [Water phase] |  |  |  |  |
| Methyl parabene | 0.4 | 0.4 | 0.4 | 0.4 |
|  | (0.2) | (0.2) | (0.2) | (0.2) |
| Purified water | 92.0 | 92.0 | 92.0 | 92.0 |
|  | (46.0) | (46.0) | (46.0) | (46.0) |
| Dipropylene glycol | 14.0 | 14.0 | 14.0 | 14.0 |
|  | (7.0) | (7.0) | (7.0) | (7.0) |

TABLE 6

Table 6: Formulation of the W/O type non-chemical UV cream unit: g
The numerals in the parenthesis indicate percentage composition unit: wt %

|  | Example 16 | Example 17 | Example 18 | Example 19 |
|---|---|---|---|---|
| [Oil phase] |  |  |  |  |
| Volatile cyclic silicone | 40.0 | 40.0 | 40.0 | 40.0 |
|  | (20.0) | (20.0) | (20.0) | (20.0) |
| Ultraviolet protective preparation (8% by weight as an ultraviolet protective powder) | 45.8 (22.9) Using Example 5 | 42.0 (21.0) Using Example 6 | 45.8 (22.9) Using Example 7 | 35.6 (17.8) Using Example 8 |
| Squalane | 2.8 | 6.6 | 2.8 | 13.0 |
|  | (1.4) | (3.3) | (1.4) | (6.5) |
| Dimethyconchopolyol | 4.0 | 4.0 | 4.0 | 4.0 |
|  | (2.0) | (2.0) | (2.0) | (2.0) |
| Organic modified montmorillonite | 1.0 | 1.0 | 1.0 | 1.0 |
|  | (0.5) | (0.5) | (0.5) | (0.5) |
| [Water phase] |  |  |  |  |
| Methyl parabene | 0.4 | 0.4 | 0.4 | 0.4 |
|  | (0.2) | (0.2) | (0.2) | (0.2) |
| Purified water | 92.0 | 92.0 | 92.0 | 92.0 |
|  | (46.0) | (46.0) | (46.0) | (46.0) |
| Dipropylene glycol | 14.0 | 14.0 | 14.0 | 14.0 |
|  | (7.0) | (7.0) | (7.0) | (7.0) |

TABLE 7

Table 7: Formulation of the W/O type non-chemical UV cream unit: g
The numerals in the parenthesis indicate percentage composition unit: wt %

|  | Example 20 | Example 21 | Example 22 |
|---|---|---|---|
| [Oil phase] |  |  |  |
| Volatile cyclic silicone | 40.0 | 40.0 | 40.0 |
|  | (20.0) | (20.0) | (20.0) |
| Ultraviolet protective preparation (8% by weight as an ultraviolet protective powder) | 43.2 (21.6) Using Example 9 | 45.8 (22.9) Using Example 10 | 42.0 (21.0) Using Example 11 |
| Squalane | 5.4 | 2.8 | 6.6 |
|  | (2.7) | (1.4) | (3.3) |
| Dimethyconchopolyol | 4.0 | 4.0 | 4.0 |
|  | (2.0) | (2.0) | (2.0) |
| Organic modified montmorillonite | 1.0 | 1.0 | 1.0 |
|  | (0.5) | (0.5) | (0.5) |
| [Water phase] |  |  |  |
| Methyl parabene | 0.4 | 0.4 | 0.4 |
|  | (0.2) | (0.2) | (0.2) |
| Purified water | 92.0 | 92.0 | 92.0 |
|  | (46.0) | (46.0) | (46.0) |
| Dipropylene glycol | 14.0 | 14.0 | 14.0 |
|  | (7.0) | (7.0) | (7.0) |

The oil phase part and the water phase part each having the formulation shown in Tables 5 to 7 were each weighted and placed in a 300 ml stainless stein and heated to 60° C. to melt. The water phase part was gradually added to the oil phase part with stirring the oil phase part at 3000 rpm by a homomixer. After the addition of the water phase was finished, the homomixer was operated at 5000 rpm for 30 minutes to make the emulsion particles uniform, followed by deaerating, filtering and cooling to obtain a non-chemical UV cream.

Comparative Examples 12 to 19

W/O type non-chemical UV creams were obtained using the formulations of raw materials shown in Tables 8 and 9 in the same manner as in Examples 12 to 22.

Comparative Example 2 and Comparative Examples 9 and 10 could not be prepared using this formulation because the content of an ultraviolet protective powder was small.

TABLE 8

Table 8: Formulation of the W/O type non-chemical UV cream unit: g
The numerals in the parenthesis indicate percentage composition unit: wt %

|  | Comparative Example 12 | Comparative Example 13 | Comparative Example 14 | Comparative Example 15 |
|---|---|---|---|---|
| [Oil phase] | | | | |
| Volatile cyclic silicone | 40.0 (20.0) | 40.0 (20.0) | 40.0 (20.0) | 40.0 (20.0) |
| Ultraviolet protective preparation (8% by weight as an ultraviolet protective powder) | 45.8 (22.9) Using Comparative Example 1 | 45.8 (22.9) Using Comparative Example 3 | 29.0 (14.5) Using Comparative Example 4 | 45.8 (22.9) Using Comparative Example 5 |
| Squalane | 2.8 (1.4) | 2.8 (1.4) | 19.6 (9.8) | 2.8 (1.4) |
| Dimethyconchopolyol | 4.0 (2.0) | 4.0 (2.0) | 4.0 (2.0) | 4.0 (2.0) |
| Organic modified montmorillonite | 1.0 (0.5) | 1.0 (0.5) | 1.0 (0.5) | 1.0 (0.5) |
| [Water phase] | | | | |
| Methyl parabene | 0.4 (0.2) | 0.4 (0.2) | 0.4 (0.2) | 0.4 (0.2) |
| Purified water | 92.0 (46.0) | 92.0 (46.0) | 92.0 (46.0) | 92.0 (46.0) |
| Dipropylene glycol | 14.0 (7.0) | 14.0 (7.0) | 14.0 (7.0) | 14.0 (7.0) |

TABLE 9

Table 9: Formulation of the W/O type non-chemical UV cream unit: g
The numerals in the parenthesis indicate percentage composition unit: wt %

|  | Comparative Example 16 | Comparative Example 17 | Comparative Example 18 | Comparative Example 19 |
|---|---|---|---|---|
| [Oil phase] | | | | |
| Volatile cyclic silicone | 40.0 (20.0) | 40.0 (20.0) | 40.0 (20.0) | 40.0 (20.0) |
| Ultraviolet diffusing preparation (8% by weight as an ultraviolet protective powder) | 45.8 (22.9) Using Comparative Example 6 | 38.0 (19.0) Using Comparative Example 7 | 32.0 (16.0) Using Comparative Example 8 | 45.8 (22.9) Using Comparative Example 11 |
| Squalane | 2.8 (1.4) | 10.6 (5.3) | 16.6 (8.3) | 2.8 (1.4) |
| Dimethyconchopolyol | 4.0 (2.0) | 4.0 (2.0) | 4.0 (2.0) | 4.0 (2.0) |
| Organic modified montmorillonite | 1.0 (0.5) | 1.0 (0.5) | 1.0 (0.5) | 1.0 (0.5) |
| [Water phase] | | | | |
| Methyl parabene | 0.4 (0.2) | 0.4 (0.2) | 0.4 (0.2) | 0.4 (0.2) |
| Purified water | 92.0 (46.0) | 92.0 (46.0) | 92.0 (46.0) | 92.0 (46.0) |
| Dipropylene glycol | 14.0 (7.0) | 14.0 (7.0) | 14.0 (7.0) | 14.0 (7.0) |

As to the resulting non-chemical UV creams, evaluation of its emulsion stability, measurement of SPF value and evaluation of its function were made. Each evaluation method will be explained in detail below.

[Evaluation of Emulsion Stability]

(1) High-Temperature Storage Stability

After each cream was stored at 50° C. for one month in a stationary condition, it was confirmed whether or not oil separation and creaming were observed. As a result, a cream that was stable was rated as ○, a cream giving rise to creaming was rated as Δ and a cream in which the oil phase was separated was rated as x.

(2) Low-Temperature Stability

After each cream was stored at 5° C. for six months in a stationary condition, it was confirmed whether or not oil separation and creaming were observed. As a result, a cream that was stable was rated as ○, a cream giving rise to creaming was rated as Δ and a cream in which the oil phase was separated was rated as x.

(3) Storage Stability Under Varied Temperatures

After each cream was stored at temperatures varied to 40° C. from −10° C. and vice versa every 24 hours for one month, it was confirmed whether or not oil separation and creaming were observed. As a result, a cream that was stable was rated as ○, a cream giving rise to creaming was rated as Δ and a cream in which the oil phase was separated was rated as x.

[Measurement of SPF]

Using UV10000S manufactured by Labsphere Company, 80 mg of a sample was applied to a transpore tape having a size of 5 cm×8 cm to measure SPF values at 10 different points and a mean value of these SPF values was taken as the SPF value.

[Functional Evaluation]

Functional evaluation of each cream was made by 20 panelists, who evaluated two items, for example, the transparent feel and extension of the cream. Specifically, 20 evaluation panelists were made to evaluate the above two items when the cream was applied to the inward part of the upper arm, to thereby giving marks according to the functional evaluation standards, and an mean value of the obtained marks of 20 panelists was calculated to accomplish the functional evaluation. The following judgment is allowed: as the mean value of the marks is closer to 4, a more excellent actual feel is obtained and as the mean value is closer to 0, a more deteriorated actual feel is obtained. The results of the functional evaluation were indicated by the following five rating marks: ◉○Δ▲x.

The standard and indication of the functional evaluation of the above two items are shown in Tables 10 and 11.

TABLE 10

Table 10: Standard and indication of the functional evaluation of a transparent feel

| | Standard of functional evaluation | | Indication of functional evaluation | |
|---|---|---|---|---|
| Marks | Details of the evaluation | Mean value of marks | Functional evaluation |
| Point 4 | A very transparent feel is felt. | 3.5-4 | ◉ |
| Point 3 | A transparent feel is felt | 3.0-3.4 | ○ |
| Point 2 | A transparent feel is slightly felt | 2.0-2.9 | Δ |
| Point 1 | A white-opaque feel is somewhat felt. | 1.0-1.9 | ▲ |
| Point 0 | A white-opaque feel is observed. | 0-0.9 | X |

TABLE 11

Table 11: Standard and indication of the functional evaluation of extension

| | Standard of functional evaluation | | Indication of functional evaluation | |
|---|---|---|---|---|
| Marks | Details of evaluation | Mean value of marks | Functional evaluation |
| Point 4 | Very easy to spread | 3.5-4 | ◉ |
| Point 3 | Easy to spread | 3.0-3.4 | ○ |
| Point 2 | Somewhat difficult to spread | 2.0-2.9 | Δ |
| Point 1 | Difficult to spread | 1.0-1.9 | ▲ |
| Point 0 | Very difficult to spread | 0-0.9 | X |

With regard to Examples 12 to 22 and Comparative Examples 12 to 19, the results of evaluation of storage stability, measurement of SPF values and functional evaluation are shown in Table 12.

TABLE 12

Table 12: Results of evaluation of storage stability, measurement of SPF values and functional evaluation

| | High-temperature storage stability (50° C.) | Low-temperature storage stability (5° C.) | Storage stability under varied temperatures (−10-40° C.) | SPF value | Transparent feel | Extension |
|---|---|---|---|---|---|---|
| Example 12 | ○ | ○ | ○ | 9.3 | ○ | ○ |
| Example 13 | ○ | ○ | ○ | 9.8 | ◉ | ◉ |
| Example 14 | ○ | ○ | ○ | 9.5 | ◉ | ◉ |
| Example 15 | ○ | ○ | ○ | 10.1 | ◉ | ◉ |
| Example 16 | ○ | ○ | ○ | 9.4 | ◉ | ◉ |
| Example 17 | ○ | ○ | ○ | 9.6 | ◉ | ◉ |
| Example 18 | ○ | ○ | ○ | 4.3 | ◉ | ◉ |
| Example 19 | ○ | ○ | ○ | 4.4 | ◉ | ◉ |

TABLE 12-continued

Table 12: Results of evaluation of storage stability, measurement of SPF values and functional evaluation

| | High-temperature storage stability (50° C.) | Low-temperature storage stability (5° C.) | Storage stability under varied temperatures (−10-40° C.) | SPF value | Transparent feel | Extension |
|---|---|---|---|---|---|---|
| Example 20 | ○ | ○ | ○ | 6.5 | ◎ | ◎ |
| Example 21 | ○ | ○ | ○ | 9.7 | ◎ | ○ |
| Example 22 | ○ | ○ | ○ | 9.4 | ◎ | ◎ |
| Comparative Example 12 | X | Δ | X | 8.2 | Δ | ◎ |
| Comparative Example 13 | Δ | ○ | Δ | 9.2 | Δ | ○ |
| Comparative Example 14 | ○ | Δ | Δ | 8.9 | ○ | Δ |
| Comparative Example 15 | X | ○ | X | 9.4 | ○ | Δ |
| Comparative Example 16 | X | ○ | X | 8.3 | Δ | Δ |
| Comparative Example 17 | X | ○ | X | 8.5 | Δ | ○ |
| Comparative Example 18 | ○ | X | X | 8.5 | Δ | Δ |
| Comparative Example 19 | X | Δ | X | 3.9 | ○ | ◎ |

As is clear from Table 12, it was confirmed that the ultraviolet protective preparation of the present invention could be formulated without impairing the functions and storage stability of cosmetics and could give a proper SPF value.

Examples 23 to 33, Comparative Examples 20 to 30

Each ultraviolet protective preparation produced in Examples 1 to 11 and Comparative Examples 1 to 11 was formulated in an amount of 10% by weight to prepare O/W emollient creams having the formulations shown in Table 13.

TABLE 13

Table 13: Formulation of O/W type UV emollient cream

| | Formulation (wt %) | Amount of formulation (g) |
|---|---|---|
| Ultraviolet protective preparation | 10.0 | 20.0 |
| Stearyl alcohol | 6.0 | 12.0 |
| Stearic acid | 2.0 | 4.0 |
| Hydrogenated lanolin | 4.0 | 8.0 |
| Octyldodecanol | 8.7 | 17.4 |
| Vitamin E | 0.1 | 0.2 |
| POE(25) cetylalcohol ether | 3.0 | 6.0 |
| Glyceryl monostearate | 2.0 | 4.0 |

TABLE 13-continued

Table 13: Formulation of O/W type UV emollient cream

| | Formulation (wt %) | Amount of formulation (g) |
|---|---|---|
| [Water phase] | | |
| 1,3-butylene glycol | 6.0 | 12.0 |
| PEG1500 | 4.0 | 8.0 |
| Methyl parabene | 0.2 | 0.4 |
| Refined water | 54.0 | 108.0 |
| Total | 100.0 | 200.0 |

The O/W type UV emollient creams were prepared as follows. The water phase was adjusted to 70° C. by heating and the oil phase was melted uniformly and adjusted to 70° C. by heating. The oil phase was gradually added to the water phase with stirring the water phase at 5000 rpm by a homomixer. After the addition was finished, the mixture was stirred for 15 minutes, then deaerated, filtered and cooled to obtain 180 g of a UV emollient cream.

As to the evaluation of the O/W type UV emollient cream, the evaluation of emulsion stability, measurement of SPF value and functional evaluation were made according to the same evaluation items and evaluation standards that were used in Examples 12 to 22 and Comparative Examples 12 to 19. The results are shown in Tables 14 and 15.

TABLE 14

Table 14: Results of evaluation of emulsion stability

| | Formulated ultraviolet protective preparation | Content of the ultraviolet protective powder (%) | High-temperature storage stability (50° C.) | Low-temperature storage stability (5° C.) | Storage stability under varied temperatures (−10-40° C.) |
|---|---|---|---|---|---|
| Example 23 | Example 1 | 2 | ○ | ○ | ○ |
| Example 24 | Example 2 | 3.5 | ○ | ○ | ○ |

TABLE 14-continued

Table 14: Results of evaluation of emulsion stability

| | Formulated ultraviolet protective preparation | Content of the ultraviolet protective powder (%) | High-temperature storage stability (50° C.) | Low-temperature storage stability (5° C.) | Storage stability under varied temperatures (−10-40° C.) |
|---|---|---|---|---|---|
| Example 25 | Example 3 | 3.5 | ○ | ○ | ○ |
| Example 26 | Example 4 | 3.5 | ○ | ○ | ○ |
| Example 27 | Example 5 | 3.5 | ○ | ○ | ○ |
| Example 28 | Example 6 | 3.8 | ○ | ○ | ○ |
| Example 29 | Example 7 | 3.7 | ○ | ○ | ○ |
| Example 30 | Example 8 | 4.5 | ○ | ○ | ○ |
| Example 31 | Example 9 | 3.7 | ○ | ○ | ○ |
| Example 32 | Example 10 | 3.5 | ○ | ○ | ○ |
| Example 33 | Example 11 | 3.8 | ○ | ○ | ○ |
| Comparative Example 20 | Comparative Example 1 | 3.5 | X | ○ | X |
| Comparative Example 21 | Comparative Example 2 | 1.0 | ○ | ○ | ○ |
| Comparative Example 22 | Comparative Example 3 | 3.5 | ○ | ○ | ○ |
| Comparative Example 23 | Comparative Example 4 | 5.5 | ○ | ○ | ○ |
| Comparative Example 24 | Comparative Example 5 | 3.5 | Δ | ○ | Δ |
| Comparative Example 25 | Comparative Example 6 | 3.5 | Δ | Δ | Δ |
| Comparative Example 26 | Comparative Example 7 | 4.2 | Δ | Δ | Δ |
| Comparative Example 27 | Comparative Example 8 | 5.0 | Δ | Δ | Δ |
| Comparative Example 28 | Comparative Example 9 | 0.9 | X | ○ | X |
| Comparative Example 29 | Comparative Example 10 | 0.6 | X | ○ | X |
| Comparative Example 30 | Comparative Example 11 | 3.5 | X | ○ | X |

TABLE 15

Table 15: Measurement of SPF value and the results of functional evaluation

| | Formulated ultraviolet protective preparation | SPF value | Transparent feel | Extension |
|---|---|---|---|---|
| Example 23 | Example 1 | 3.4 | ○ | ◎ |
| Example 24 | Example 2 | 5.6 | ◎ | ◎ |
| Example 25 | Example 3 | 5.5 | ◎ | ◎ |
| Example 26 | Example 4 | 5.8 | ◎ | ◎ |
| Example 27 | Example 5 | 5.5 | ◎ | ◎ |
| Example 28 | Example 6 | 6.1 | ◎ | ◎ |
| Example 29 | Example 7 | 2.9 | ◎ | ◎ |
| Example 30 | Example 8 | 3.2 | ◎ | ◎ |
| Example 31 | Example 9 | 4.3 | ◎ | ◎ |
| Example 32 | Example 10 | 5.6 | ◎ | ○ |
| Example 33 | Example 11 | 6.0 | ◎ | ◎ |
| Comparative Example 20 | Comparative Example 1 | 4.9 | Δ | ○ |
| Comparative Example 21 | Comparative Example 2 | 1.5 | Δ | Δ |
| Comparative Example 22 | Comparative Example 3 | 6.3 | Δ | ○ |
| Comparative Example 23 | Comparative Example 4 | 8.4 | Δ | ○ |
| Comparative Example 24 | Comparative Example 5 | 5.0 | ○ | Δ |
| Comparative Example 25 | Comparative Example 6 | 4.8 | Δ | Δ |
| Comparative Example 26 | Comparative Example 7 | 5.3 | Δ | ○ |
| Comparative Example 27 | Comparative Example 8 | 7.0 | Δ | ○ |
| Comparative Example 28 | Comparative Example 9 | 1.3 | ◎ | ○ |
| Comparative Example 29 | Comparative Example 10 | 1.1 | ◎ | ○ |
| Comparative Example 30 | Comparative Example 11 | 2.5 | ◎ | ○ |

As is clear from Tables 14 and 15, it was confirmed that the ultraviolet protective preparation of the present invention could be formulated without impairing the function and storage stability of a cosmetic and could give a proper SPF value.

The invention claimed is:

1. A method for producing a cosmetic comprising a step of adding 3 to 95% by weight of an ultraviolet protective preparation comprising 0.2 to 3% by weight of an ester compound, 52 to 79.9% by weight of an ester oil and 15 to 45% by weight of an ultraviolet protective powder to an oil phase of a cosmetic formulation, wherein the ester compound is an ester compound produced from glycerin, behenic acid and eicosanic diacid and the ester oil is an oil agent which has a liquid or paste form at normal temperature and is one or more ester oils prepared from one or more polyols selected from neopentyl glycol, 2-methyl-2-ethyl-1,3-propanediol, glycerin, trimethylolpropane, diglycerin, ditrimethylolpropane, erythritol and pentaerythritol and one or more saturated straight-chain carboxylic acids having a monovalent carboxyl group and/or saturated branched carboxylic acids having a monovalent carboxyl group.

2. The method according to claim 1, wherein the cosmetic is one type selected from face lotions, milky lotions, creams, ointments, foundations, lip creams, lipsticks, mascaras, eye shadows, eyebrows, nail enamels and cheek colors.

3. The method according to claim 1, wherein the ester compound is an ester compound produced from glycerin, behenic acid and eicosanic diacid,
the ester oil is at least one of neopentyl glycol dicaprate, glyceryl tri-2-ethylhexanoate or pentaerythritol tetra-2-ethylhexanoate, and
the ultraviolet protective powder is at least one of titanium dioxide, iron-containing titanium dioxide or zinc oxide.

4. The method according to claim 3, wherein the ultraviolet protective preparation further comprising lecithin.

5. The method according to claim 1, wherein the amount of the ester compound to be formulated is 0.4 to 2% by weight, the amount of the ester oil to be formulated is 57.1 to 74.8% by weight and the amount of the ultraviolet protective powder to be formulated is 24.8 to 39.9% by weight.

6. The method according to claim 1, wherein the ester oil has a viscosity of 4 to 100 mPa·s at 20° C.

7. The method according to claim 1, wherein the ester oil is one or more of neopentyl glycol dicaprate, glyceryl tri-2-ethylhexanoate and pentaerythritol tetra-2-ethyl hexanoate.

8. The method according to claim 1, wherein the ultraviolet protective powder is one or more powders selected from the group consisting of titanium dioxide, iron-containing titanium dioxide and zinc oxide.

9. The method according to claim 1, wherein the ultraviolet protective preparation further comprising lecithin.

10. The method according to claim 9, wherein the lecithin is a hydrogenated lecithin.

11. The method according to claim 1, wherein the ratio by weight of lecithin is 0.0001 to 0.05 to the total amount when the total amount of the ester compound, the ester oil and the ultraviolet protective powder is set to 1.

12. The method according to claim 1, wherein the ultraviolet protective preparation has a storage elastic modulus (G') when a shear stress ($\tau$) of 0.1 to 10 Pa is applied at a frequency of 1 Hz at 25° C. is 10 to 5000 Pa and a loss elastic modulus (G") when a shear stress ($\tau$) of 0.1 to 10 Pa is applied at a frequency of 1 Hz at 25° C. is 80 to 3000 Pa.

13. The method according to claim 1, wherein the ultraviolet protective preparation has an area enclosed by the shear rate and shear stress measured at 25° C. in a hysteresis loop is 300 to 3000 Pa×1/s.

* * * * *